(12) United States Patent
Silver et al.

(10) Patent No.: US 11,350,966 B2
(45) Date of Patent: Jun. 7, 2022

(54) SYSTEM AND METHOD FOR CONTROLLING GAS COMPOSITION IN A SURGICAL CAVITY DURING ENDOSCOPIC SURGICAL PROCEDURES

(71) Applicant: Conmed Corporation, Utica, NY (US)

(72) Inventors: Mikiya Silver, New Haven, CT (US); Gary Tegan, Edina, MN (US)

(73) Assignee: Conmed Corporation, Largo, FL (US)

(*) Notice: Subject to any disclaimer, the term of this patent is extended or adjusted under 35 U.S.C. 154(b) by 585 days.

(21) Appl. No.: 16/000,378

(22) Filed: Jun. 5, 2018

(65) Prior Publication Data
US 2019/0365414 A1    Dec. 5, 2019

(51) Int. Cl.
*A61B 17/34*    (2006.01)
*A61M 13/00*    (2006.01)
(Continued)

(52) U.S. Cl.
CPC ...... *A61B 17/3423* (2013.01); *A61B 17/3474* (2013.01); *A61B 17/3462* (2013.01);
(Continued)

(58) Field of Classification Search
CPC ............ A61B 17/3423; A61B 17/3474; A61B 2017/00238; A61B 2090/064; A61B 2017/00544; A61B 17/3462; A61B 17/3498; A61B 2218/006; A61B 1/3132; A61B 1/313; A61B 18/1482; A61B 13/00;
(Continued)

(56) References Cited

U.S. PATENT DOCUMENTS 5,360,396 A * 11/1994 Chan ................... A61M 13/003
                                                         600/560
5,676,155 A * 10/1997 Novak ................ A61M 13/003
                                                         600/560
(Continued)

FOREIGN PATENT DOCUMENTS

JP    2017-205342 A    11/2017
WO    2017/122188 A1    7/2017
WO    2017/214193 A1   12/2017

OTHER PUBLICATIONS

NASA. (Mar. 20, 2009). Mass flow rate. NASA. https://www.grc.nasa.gov/WWW/k-12/airplane/mflow.html. (Year: 2009).*

(Continued)

*Primary Examiner* — Nilay J Shah
(74) *Attorney, Agent, or Firm* — Locke Lord LLP; Scott D. Wofsy; Joshua L. Jones (57) ABSTRACT

A method for controlling gas composition in a surgical cavity during an endoscopic surgical procedure includes monitoring for a plurality of gas species in a gas flow from a surgical cavity of a patient. The method includes measuring the plurality of gas species in the gas flow from the surgical cavity and determining if the gas species measured in the gas flow from the surgical cavity are each present and/or within a respective desired range. The method includes adding gas into the surgical cavity if one or more gas species in the plurality of gas species is outside of the respective desired range so as to bring a composition of gas species in the surgical cavity within the respective desired range.

22 Claims, 9 Drawing Sheets

(51) Int. Cl.
*A61B 17/00* (2006.01)
*A61B 90/00* (2016.01)

(52) U.S. Cl.
CPC . *A61B 17/3498* (2013.01); *A61B 2017/00238* (2013.01); *A61B 2017/00544* (2013.01); *A61B 2090/064* (2016.02); *A61M 13/006* (2014.02); *A61M 2202/0225* (2013.01); *A61M 2205/3344* (2013.01)

(58) Field of Classification Search
CPC ............... A61B 13/003; A61B 13/006; A61B 2202/0283; A61B 2202/0266; A61B 2202/0291; A61M 2205/3344; A61M 2202/0225; A61M 13/006; A61M 16/161; A61M 2016/102; A61M 2016/103; A61M 2205/3334
See application file for complete search history.

(56) References Cited

U.S. PATENT DOCUMENTS

| | | | | |
|---|---|---|---|---|
| 6,158,434 | A * | 12/2000 | Lugtigheid | A61M 16/12 128/204.22 |
| 7,704,223 | B2 * | 4/2010 | Mantell | A61M 13/003 604/24 |
| 7,854,724 | B2 | 12/2010 | Stearns et al. | |
| 7,938,793 | B2 * | 5/2011 | Mantell | A61M 13/003 604/26 |
| 8,172,836 | B2 * | 5/2012 | Ward | A61B 18/1206 606/34 |
| 8,715,219 | B2 | 5/2014 | Stearns et al. | |
| 8,961,451 | B2 | 2/2015 | Stearns et al. | |
| 9,067,030 | B2 | 6/2015 | Stearns et al. | |
| 9,295,490 | B2 | 3/2016 | Stearns et al. | |
| 9,375,539 | B2 | 6/2016 | Stearns et al. | |
| 9,480,795 | B2 * | 11/2016 | Uhland | A61M 5/16836 |
| 9,521,963 | B2 * | 12/2016 | Esposito | A61B 5/097 |
| 9,526,849 | B2 | 12/2016 | Stearns et al. | |
| 9,526,886 | B2 | 12/2016 | Mastri et al. | |
| 9,950,127 | B2 | 4/2018 | Stearns et al. | |
| 10,010,266 | B2 * | 7/2018 | Hestness | A61B 17/0218 |
| 2005/0123588 | A1 * | 6/2005 | Zhu | A61L 26/0066 424/443 |
| 2007/0077200 | A1 * | 4/2007 | Baker | A61M 16/12 424/9.1 |
| 2012/0136269 | A1 * | 5/2012 | Weckstrom | A61M 16/0833 600/532 |
| 2012/0330224 | A1 * | 12/2012 | Mailova | A61K 33/00 604/24 |
| 2013/0096399 | A1 * | 4/2013 | Scalici | A61B 5/4255 600/309 |
| 2013/0181169 | A1 * | 7/2013 | Klein | C01B 3/384 252/373 |
| 2014/0031814 | A1 | 1/2014 | Deutscher et al. | |
| 2014/0303615 | A1 * | 10/2014 | Amoah | B03C 3/38 606/34 |
| 2014/0358077 | A1 * | 12/2014 | Oruklu | A61M 5/1684 604/111 |
| 2015/0174305 | A1 * | 6/2015 | Bharat | A61M 1/0013 604/26 |
| 2015/0226585 | A1 * | 8/2015 | Yang | G01D 11/245 73/431 |
| 2016/0287817 | A1 * | 10/2016 | Mastri | A61M 5/165 |
| 2016/0317081 | A1 | 11/2016 | Huang | |
| 2017/0000959 | A1 * | 1/2017 | Mantell | A61M 13/003 |
| 2017/0274160 | A1 * | 9/2017 | Mantell | A61M 39/24 |
| 2018/0132895 | A1 | 5/2018 | Silver | |
| 2018/0133416 | A1 * | 5/2018 | Silver | A61M 13/006 |

OTHER PUBLICATIONS

Price, R. (Mar. 12, 2014). Rmp lecture notes. http://facstaff.cbu.edu/rprice/lectures/compos.html. (Year: 2014).*
International Search Report issued in corresponding PCT Patent Application No. PCT/US2019/031048, dated Aug. 19, 2019.
Extended European Search Report issued in EP 19814610.2, dated Feb. 4, 2022.

* cited by examiner

SYSTEM AND METHOD FOR CONTROLLING GAS COMPOSITION IN A SURGICAL CAVITY DURING ENDOSCOPIC SURGICAL PROCEDURES

BACKGROUND OF THE INVENTION

1. Field of the Invention

The subject disclosure is directed to endoscopic surgery, and more particularly, to a system and method for controlling gas composition in a surgical cavity during an endoscopic or laparoscopic surgical procedure.

2. Description of Related Art

Laparoscopic or "minimally invasive" surgical techniques have become commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal cavity with a pressurized fluid, such as carbon dioxide, to create an operating space, which is referred to as a pneumoperitoneum. The insufflation can be carried out by a surgical access device, such as a trocar, equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which can be made with the surgical access devices themselves, often using a separate inserter or obturator placed therein. Following insertion, the obturator is removed, and the trocar allows access for instruments to be inserted into the abdominal cavity. Typical trocars provide a pathway to insufflate the abdominal cavity, so that the surgeon has an open interior space in which to work.

The trocar must also provide a way to maintain the pressure within the cavity by sealing between the trocar and the surgical instrument being used, while still allowing at least a minimum amount of freedom of movement for the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas from the abdominal cavity. These sealing mechanisms often comprise a duckbill-type valve made of a relatively pliable material, to seal around an outer surface of surgical instruments passing through the trocar.

SurgiQuest, Inc., a wholly owned subsidiary of ConMed Corporation has developed unique gas sealed surgical access devices that permits ready access to an insufflated surgical cavity without the need for conventional mechanical valve seals, as described, for example, in U.S. Pat. No. 7,854,724. These devices are constructed from several nested components including an inner tubular body portion and a coaxial outer tubular body portion. The inner tubular body portion defines a central lumen for introducing conventional laparoscopic surgical instruments to the abdominal cavity of a patient and the outer tubular body portion defines an annular lumen surrounding the inner tubular body portion for delivering insufflation gas to the abdominal cavity of the patient and for facilitating periodic sensing of abdominal pressure. SurgiQuest, Inc, has also developed multimodal insufflation systems such as those described in U.S. Pat. Nos. 8,715,219, 8,961,451, and 9,295,490 as well as smoke evacuation systems such as those described in U.S. patent application Ser. No. 15/945,007 filed Apr. 4, 2018 the contents of each of which are incorporated by reference herein in their entireties.

These unique surgical access devices are utilized with a gas delivery system such as the gas delivery systems described above that provides a flow of pressurized surgical gas to the central lumen of a trocar to create and maintain the gas seal. The central lumen of the access device is in direct communication with the body cavity and thus the recirculating flow will necessarily comprise the gas within the body cavity. This gas is continuously recirculated without impacting the insufflation and sensing through the annular lumen. During the process of a surgical procedure, the components of gas within the body cavity can change as a result of electrocautery, anesthesia, and the like. This gas composition can impact the patient but in the state of the art, there is no reliable way of knowing what changes are occurring in gas composition within the body cavity during a surgical procedure.

Although early insufflation was done with air, nitrogen, or other gases and blends, beginning in the 1970s carbon dioxide began becoming the standard of care choice for insufflation gas. Carbon dioxide has numerous benefits over other gases that are recognized by the medical and scientific communities. The human body naturally has built-in methods of clearing carbon dioxide. During respiration, oxygen-rich air is inhaled and oxygen is transported throughout the body via the arterial system. Carbon dioxide is a naturally-occurring waste product from cellular respiration, and is transported via the venous system back to the lungs to be exhaled. Carbon dioxide is readily absorbed by the body and can be cleared via the aforementioned method. Other gases are more difficult to clear from the body, which can lead to post-operative complications including emphysema or trapped insufflation gas from incomplete desufflation, subcutaneous emphysema (gas trapped under the skin), or embolism. Embolisms can occur when gas bubbles enter the blood stream and block off blood flow in a particular vessel. Embolisms can lead to nerve, muscle, or brain damage or even death. Due to the ability for the human body to clear carbon dioxide, gas bubbles of carbon dioxide are less likely to cause a damaging embolism than other gases as the body can more easily absorb the carbon dioxide to reduce the size or eliminate the embolism.

As minimally invasive surgery proliferated and insufflation in the laparoscopic cavity became commonplace, insufflation began to be used in other endoscopic procedures such as colonoscopies and minimally invasive colorectal surgery. Early studies and publications that explored insufflation in the colorectal cavity showed particular concern with the topic of combustion. In laparoscopic and other endoscopic surgeries, the use of electrocautery device to cut and coagulate soft tissue is commonplace. Monopolar, bipolar, RF, harmonic, and other devices are readily available in the market. These devices use electricity or other energy forms to burn tissue as incisions are made to prevent excess bleeding. Colorectal surgeons became concerned with air insufflation, as the potential presence of trapped pockets of methane gas in patients' bowels could provide fuel for combustion. The presence of oxygen in air insufflation was found to support explosions that occurred in several noted cases. The fact that carbon dioxide is not combustible quickly led to its adoption within the medical community as the insufflation gas of choice and standard of care in colorectal insufflation.

Those skilled in the art of minimally-invasive surgeries may understand that a variety of other gases may enter the surgical cavity from a variety of sources. Room air may enter the cavity from leakages or via gas trapped in sterile tubesets or other medical products pneumatically sealed in sterile packaging and then inserted or attached to the patient cavity. Electrocautery or lasercautery devices themselves (such as Argon Beam Coagulators) occasionally use certain gases like Argon to transmit their energy and can lead to a presence of that gas in the cavity. The process of cautery can release carbon monoxide and volatile organic compounds (VOCs) that are harmful gaseous compounds trapped in the cavity. Finally, certain gases are used to anesthetize patients before operating. These anesthesia gases can be metabolized by the body and show presence in the surgical cavity. This is another example of how non-carbon dioxide gas can be problematic in surgical cavities.

While the foregoing discussion makes particular mention of laparoscopy and colorectal insufflation, those skilled in the art will readily appreciate that the issue of controlling gas composition in surgical cavities is generally relevant for insufflation of any suitable surgical cavity, including thoracic insufflation, and for any suitable endoscopic procedure.

The conventional techniques have been considered satisfactory for their intended purpose. However, there is an ever present need for improved systems and methods for controlling gas delivery during surgical procedures. This disclosure provides a solution for this need.

SUMMARY OF THE DISCLOSURE

A method for controlling gas composition in a surgical cavity during an endoscopic surgical procedure includes monitoring for a plurality of gas species in a gas flow from a surgical cavity of a patient. The method includes measuring the plurality of gas species in the gas flow from the surgical cavity and determining if the gas species measured in the gas flow from the surgical cavity are each present and/or within a respective desired range. The method includes taking corrective action in any of the gas species are outside the respective desired range.

Taking corrective action can include adding gas into the surgical cavity if one or more gas species in the plurality of gas species is outside of the respective desired range so as to bring a composition of gas species in the surgical cavity within the respective desired range. Taking corrective action can include warning a user of non-ideal gas composition. Taking corrective action can include instructing an external or internal insufflator to flush the surgical cavity with carbon dioxide. Taking corrective action can include disabling a device to prevent harm to the patient. Gas sensors may measure mass flow rates or volumetric flow rates in order to measure the presence of different gas species. The system/method may include the use of a look-up table to calculate molar percentages from a plurality of mass flow or volumetric flow readings. Taking corrective action can include delivering a flow of gas into the surgical cavity from an insufflator or gas recirculator.

Monitoring for a plurality of gas species in a gas flow from the surgical cavity can involve continuously monitoring the flow of gas. Monitoring for a plurality of gas species in a gas flow from the surgical cavity can involve continuously or periodically sampling the flow of gas. The gas flow from the surgical cavity can result from evacuating gas from the surgical cavity, from recirculating gas from the surgical cavity, and/or from intermittently leaking gas from the surgical cavity. Adding gas into the surgical cavity can involve delivering a flow of gas into the surgical cavity from an insufflator or gas recirculator.

Determining if the gas species measured in the gas flow from the surgical cavity are each within a respective desired range can involve determining if the composition of gas species includes a concentration of Carbon Dioxide ($CO_2$) that is below a specified level. Adding gas into the surgical cavity can involve adding Carbon Dioxide ($CO_2$) into the surgical cavity if the concentration of Carbon Dioxide ($CO_2$) is below the specified level so to increase the concentration of Carbon Dioxide ($CO_2$) in the surgical cavity above the specified level.

Monitoring for a plurality of gas species and determining if the gas species measured can include monitoring for and determining if Nitrogen ($N_2$), Oxygen ($O_2$), Nitrous Oxide ($N_2O$), water vapor ($H_2O$), Sevoflurane, Methane ($CH_4$), Xenon (Xe), Argon (Ar), Desflurane, Isoflurane, and/or Carbon Monoxide (CO) is present and/or within a respective desired range.

Measuring the plurality of gas species in the gas flow can include calculating each gas species as a molar percentage by summing flow rates of individual gas species based on information from a plurality of gas species sensors and dividing by total flow rate for all gas species in the gas flow. Calculating each gas species can include calculating each gas species as a molar percentage by summing flow rates of individual gas species based on information from a plurality of gas species sensors and dividing by total flow rate for all gas species in the gas flow.

Monitoring can include using a sensor that is positioned in line with a main gas flow coming from the surgical cavity. It is also contemplated that monitoring can include using a sensor that is positioned to sample from a stream of gas flow parallel with a main gas flow coming from the surgical cavity.

A system for controlling gas composition in a surgical cavity during an endoscopic surgical procedure includes a sensor for monitoring a plurality of gas species in a gas flow from a surgical cavity of a patient. A processor is operatively connected to the sensor for determining if the gas species monitored in the gas flow from the surgical cavity are each present and/or within a respective desired range and taking corrective action if any gas species are outside the respective desired range.

An insufflator can be operatively connected to the processor for adding gas into the surgical cavity if one or more gas species in the plurality of gas species is outside of the respective desired range so as to bring a composition of gas species in the surgical cavity within the respective desired range for a desired composition.

The sensor can include at least one of a mass flow sensor, a nondispersive infrared sensor, a metal oxide sensor, a catalytic bead sensor, a thermal conductivity sensor, a colorimetric sensor, a photoionization detector, a flame ionization detector, an electrochemical sensor, and/or a semiconductor sensor and an acoustic wave sensor. The sensor can include an array of gas species sensors. The array of gas species sensors can be arranged in parallel. It is also contemplated that the array of gas species sensors can be arranged in series.

A pump can be operatively connected to the insufflator to move the flow of gas from the surgical cavity. The pump can be operatively connected to at least one trocar. The insufflator can be operatively connected to a source of gas.

The sensor for monitoring for a plurality of gas species can include one or more gas species sensors sensitive to concentration of Carbon Dioxide ($CO_2$), Nitrogen ($N_2$), Oxygen ($O_2$), Nitrous Oxide ($N_2O$), water vapor ($H_2O$), Sevoflurane, Methane ($CH_4$), Xenon (Xe), Argon (Ar), Desflurane, Isoflurane, and/or Carbon Monoxide (CO).

These and other features of the subject disclosure will become more readily apparent to those having ordinary skill in the art to which the subject disclosure appertains from the detailed description of the preferred embodiments taken in conjunction with the following brief description of the drawings.

BRIEF DESCRIPTION OF THE DRAWINGS

So that those skilled in the art will readily understand how to make and use the gas circulation system of the subject disclosure without undue experimentation, preferred embodiments thereof will be described in detail herein below with reference to the figures wherein.

DETAILED DESCRIPTION OF THE PREFERRED EMBODIMENTS

Figure 1:
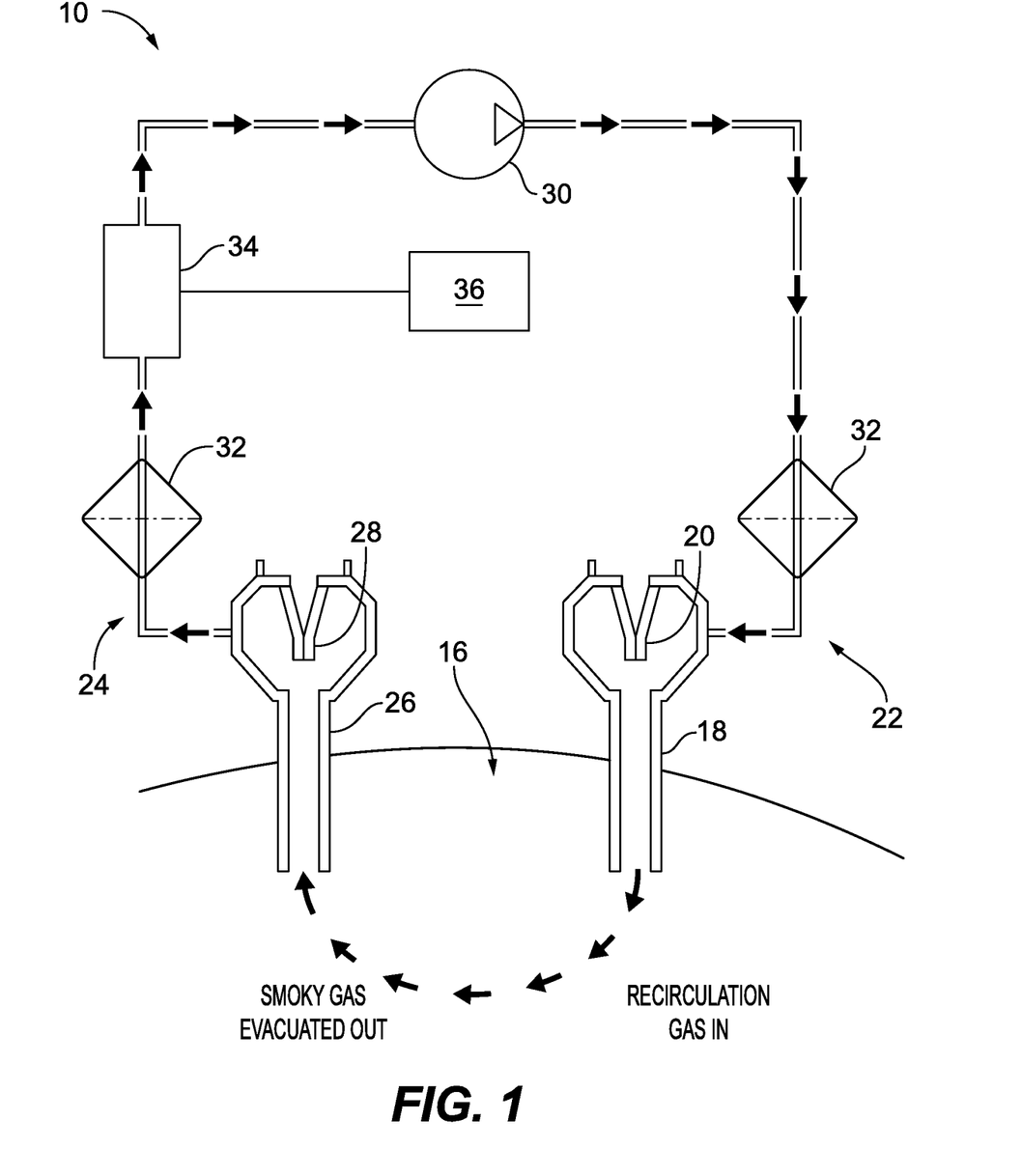
FIG. 1 is a schematic illustration of a surgical gas recirculation and filtration system constructed in accordance with an embodiment of the subject disclosure which is configured for monitoring gas species in a flow of gas from a surgical cavity.

Reference will now be made to the drawings wherein like reference numerals identify similar structural features or aspects of the subject disclosure. For purposes of explanation and illustration, and not limitation, a partial view of an exemplary embodiment of a surgical gas delivery system in accordance with the disclosure is shown in FIG. 1 and is designated generally by reference character 10. Other embodiments of surgical gas delivery systems in accordance with the disclosure, or aspects thereof, are provided in FIGS. 2-9B, as will be described. The systems and methods described herein can be used for controlling gas composition in a surgical cavity during an endoscopic surgical procedure.

Referring now to FIG. 1, there is illustrated a gas evacuation system 10, and more particularly a gas recirculation and smoke evacuation system, for continuously removing gas from a surgical cavity 16 of a patient during an endoscopic surgical procedure. Smoke evacuation system 10 includes an inlet flow path 22 leading to a first trocar 18 communicating with the surgical cavity 16 of a patient, through which a continuous flow of gas is delivered to the surgical cavity 16. The first trocar 18 is preferably a standard trocar with a mechanical seal 20, as opposed to a gas sealed trocar. The system 10 further includes an outlet flow path 24 leading from a second trocar 26 communicating with the surgical cavity 16, though which a continuous flow of smoky gas is removed from the surgical cavity 16. The second trocar 26 is also preferably a standard trocar with a mechanical seal 28. While shown and described herein in the exemplary context of mechanically sealed trocars, those skilled in the art will readily appreciate that systems and methods as disclosed herein can be used with pneumatically sealed and/or mechanically sealed trocars without departing from the scope of this disclosure.

A pump 30 communicates with the inlet flow path 22 for delivering a continuous flow of clean gas to the surgical cavity 16 and with the outlet flow path 24 for removing a continuous flow of smoky gas from the surgical cavity 16. Those skilled in the art will readily appreciate that continuous flow is used here as an example, and that it is not necessary for flow to be continuous within the scope of this disclosure.

A filter 32 is operatively associated with at least one of the inlet flow path 22 and the outlet flow path 24, for cleaning or otherwise conditioning the gas passing therethrough. A sensor 34 is included in the outlet flow path 24 upstream of the pump 30 and downstream of the filter 32 and second trocar 26. The sensor 34 is configured for monitoring a plurality of gas species in the gas flow from a surgical cavity 16 of a patient. A processor 36 is operatively connected to the sensor 34 for determining if the gas species monitored in the gas flow from the surgical cavity 16 are each present and/or within a respective desired range.

The sensor 34 can include at least one of a mass flow sensor, a nondispersive infrared sensor, a metal oxide sensor, a catalytic bead sensor, a thermal conductivity sensor, a colorimetric sensor, a photoionization detector, a flame ionization detector, an electrochemical sensor, a semiconductor sensor and an acoustic wave sensor, and/or any other suitable type of gas sensor. The sensor 34 can include one or more gas species sensors sensitive to concentration of Carbon Dioxide ($CO_2$), Nitrogen ($N_2$), Oxygen ($O_2$), Nitrous Oxide ($N_2O$), water vapor ($H_2O$), Sevoflurane, Methane ($CH_4$), Xenon (Xe), Argon (Ar), Desflurane, Isoflurane, Carbon Monoxide (CO), and/or any other suitable gas species.

Figure 2:
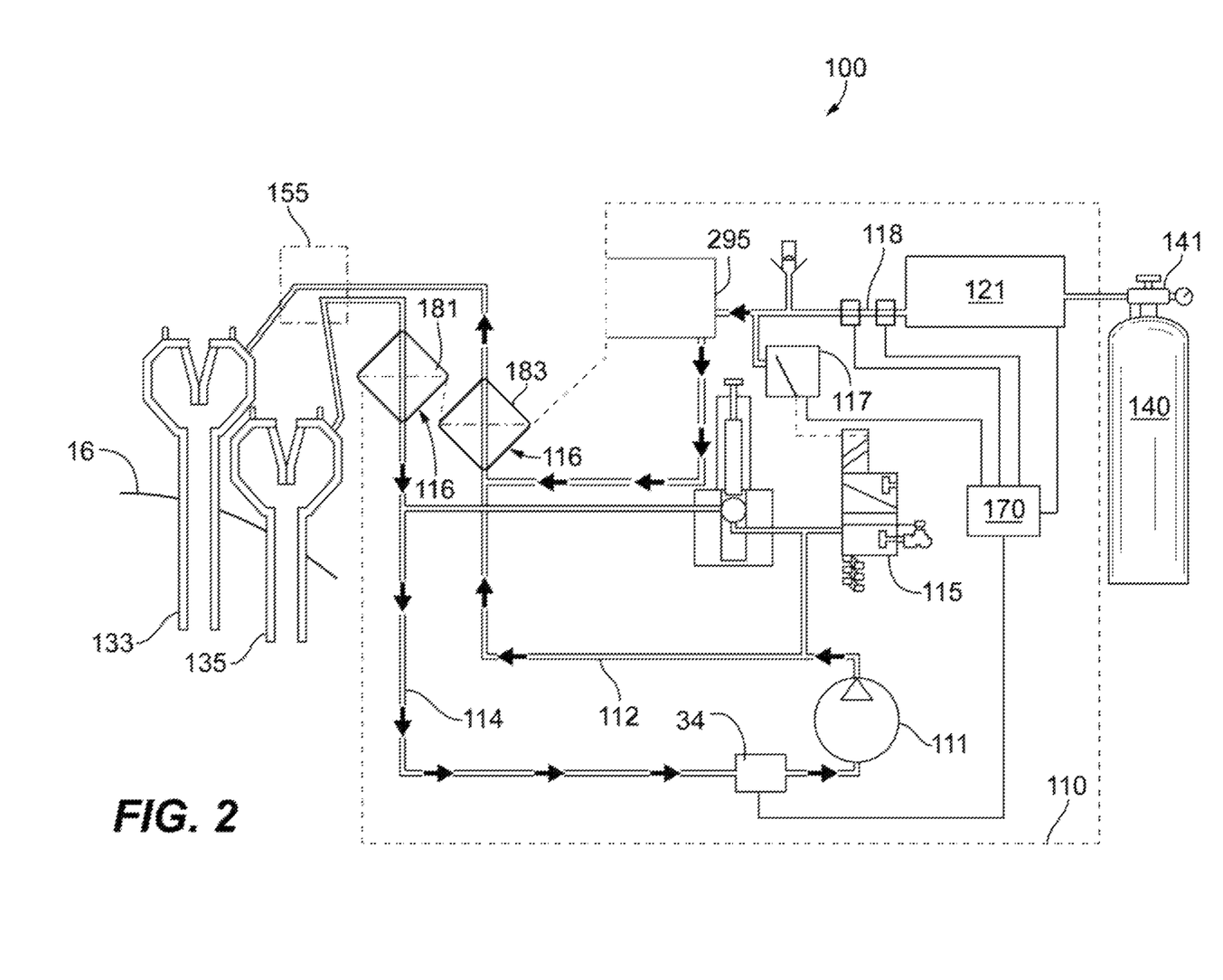
FIG. 2 is a schematic illustration of a surgical gas delivery system constructed in accordance with another embodiment of the subject disclosure which is configured for continuous monitoring of gas species in a flow of gas from a surgical cavity during smoke evacuation with an integrated insufflator.

With reference now to FIG. 2, another exemplary embodiment of a system 100 for controlling gas composition in a surgical cavity is shown as a smoke evacuator with integrated insufflator. The system 100 includes three conduits 112, 114, 118 leading from other active internal system components and a valve 295 that enables conduit 118 to supply and combine with conduit 112. Conduits 112 and 114 lead, respectively, to two different surgical devices 133, 135.

The valve 295 is provided integrally within the control unit 110 as indicated schematically by placement of the broken line reference number 110. The valve 295 is provided with two operating positions—positions, A and B, corresponding to different functions, as described below. When the pressure sensing function of the system 100 is active, the valve 295 is positioned in, position "A", permitting connection of the insufflation/sensing conduit 118 to conduit 112 therethrough, through the tube set 155 to the surgical device 133 (e.g., a trocar). When the valve 295 is positioned at position A and connects the surgical device 133, the insufflation subunit 121 is permitted to sense the abdominal pressure. A pump 111 is operatively connected to the insufflator and the surgical device 133 to move the flow of gas from the surgical cavity 16. In position A of valve 295, output from the pump 111 enters the supply conduit 114. This configuration allows the pump 111 to continue running during sensing and thus avoids any power spikes which might occur if stopping and restarting of the pump 111.

If the system 100 is set to a suitable mode (such as combined smoke evacuation and insufflation), when the surgical cavity pressure is determined through sensing, the valve 295 is switched to position A in order to connect the recirculation conduit 112 to the insufflator conduit 118, permitting addition of insufflation gas into the system 100 through the recirculation conduit 112. Concurrently, the insufflation subunit 121 can be set to insufflating mode only, therefore only adding gas to the system 100 and not sensing pressures. While in position A, the valve 295 permits the function of the insufflation subunit 121 alone—switching from sensing to supplying carbon dioxide—as is performed in conventional surgical insufflators, in accordance with a preferred aspect.

Accordingly, as described above, in system 100 of FIG. 2, smoke evacuation and filtration is only performed when the valve 295 is in position B, which permits the recirculation of gas via pump 111 to the surgical cavity 16. In such an arrangement, toggling to and from smoke evacuation/filtration and pressure sensing can be configured as either a normally sensing mode, or as a normally filtering mode, as desired or required. A normally sensing mode is likely to be preferred over a normally filtering mode, as monitoring of abdominal pressures is typically a priority.

In certain applications, it is advantageous to monitor pressure at the surgical cavity 16, in real time, during insufflation. Real time pressure monitoring helps to better detect and respond to changes in pressure the surgical cavity. Furthermore, continuous pressure monitoring in conjunction with the consistent flow of new or recirculated insufflation gas also facilitate improved smoke removal from the surgical cavity.

Those skilled in the art will readily appreciate that system 100 can be used for real-time sensing smoke evacuation, additional details of which are described in U.S. patent application Ser. No. 15/945,007, which is incorporated by reference herein in its entirety.

Similar to system 10 described above, system 100 includes a sensor 34 in the flow path 114 just upstream of the pump 111 for monitoring a plurality of gas species in the gas flow from the surgical cavity 16. An insufflator, e.g., the insufflation unit 121, is operatively connected to the processor 170 for adding gas from a supply source 140 into the surgical cavity 16 if one or more gas species in the plurality of gas species is outside of the respective desired range so as to bring a composition of gas species in the surgical cavity 16 within the respective desired range. A dump valve 115 is in included in connection with the conduit 114. Sensor 117 is in fluid communication with the insufflation conduit 118 or other source of abdominal pressure. When an overpressure condition is sensed, the pressure sensor 117 signals the dump valve 115 to release fluid out of the system 100.

Figure 3:
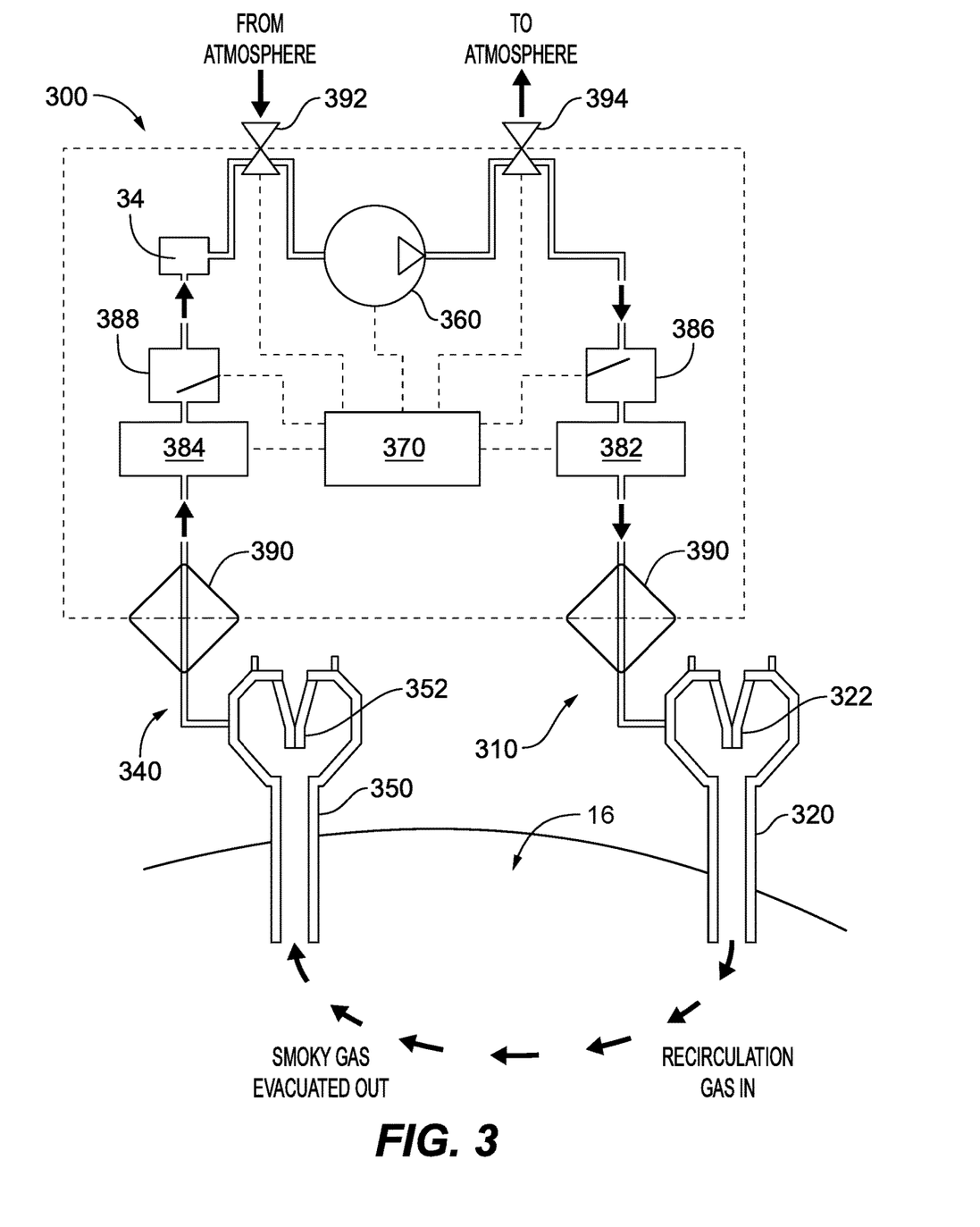
FIG. 3 is a schematic illustration of a surgical gas delivery system constructed in accordance with another embodiment of the subject disclosure which is configured for continuous monitoring of gas species in a flow of gas from a surgical cavity during gas recirculation and/or smoke evacuation with venting.

With reference now to FIG. 3, another exemplary embodiment of a system 300 for controlling gas composition in a surgical cavity is shown as a gas recirculation/smoke evacuation system with venting. System 300 includes trocars 320 and 350, seals 322 and 352, and filters 390 similar to those described above with reference to FIG. 1. The embodiment of the system 300 may be configured so that the gas flow rate, supplied at a programmed driving pressure, varies depending upon a surgical cavity pressure within the surgical cavity 16 and the processor 370 is configured to determine the surgical cavity pressure corresponding to a gas flow rate measurement continuously measured by a flow sensor communicating with processor 370, such as, for example, the flow sensor 382 operatively associated with the inlet flow path 310 and/or the flow sensor 384 operatively associated with the outlet flow path 340. A typical driving pressure for a smoke evacuation system of this type is about 60 mmHg.

The embodiment of system 300 may be configured so that a driving pressure required to maintain a specified gas flow rate varies depending upon a surgical cavity pressure in surgical cavity 16 and the processor 370 is configured to determine the surgical cavity pressure corresponding to a measured driving pressure continuously measured by a pressure sensor communicating with processor 370, such as, for example, the pressure sensor 386 operatively associated with the inlet flow path 310 and/or the pressure sensor 388 operatively associated with the outlet flow path 340. A typical gas flow rate for a smoke evacuation system of this type is about 5 L/min.

A processor 370 controls the pump 360 in such a manner so that clean gas is delivered to the surgical cavity 16 by the pump 360 at a gas flow rate that relates to the gas flow rate at which smoky gas is removed from the surgical cavity 16 by the pump 360. For example, the processor 370 controls the pump 360 in such a manner so that clean gas is delivered to the surgical cavity 16 by the pump 360 at a gas flow rate that is equal to the gas flow rate at which smoky gas is removed from the surgical cavity 16 by the pump 360, or at a gas flow rate that is greater than or less than the gas flow rate at which smoky gas is removed from the surgical cavity 16 by the pump 360, in the event of an under-pressure condition or an over-pressure condition in the surgical cavity 16. In this regard, it should be understood that while the flow of gas throughout this system is essentially continuous, there may be circumstances in which the insufflation or gas delivery flow rate and/or the evacuation or gas removal flow rate could temporarily drop to 0 L/min, in order to prevent extreme under or over pressure conditions in the system. It is also contemplated that system 300 can be configured to communicate with an external insufflator that monitors cavity pressure and insufflates with fresh carbon dioxide.

Optionally, a valve 392 may be located on the inlet side (340) of the pump 360 that would be controlled by the processor 370 to draw in more gas from atmosphere and/or a valve 394 may be located on the outlet side (310) of the pump 360 that would be controlled by the processor 370 to bleed off some of the gas flow to atmosphere in order to better adjust the flow rate.

Similar to system 10 described above, system 300 includes a sensor 34 in the flow path 340 just upstream of the valve 392 and pump 360 and just downstream from flow sensor 384 for monitoring a plurality of gas species in the gas flow from the surgical cavity 16. Sensor 34 is operatively connected to the processor 370 for control of gas composition in the surgical cavity 16. System 300 can use the valves 392, 394 to bleed off unwanted gas species if the sensor 34 reads presence and/or concentration of a potentially harmful gas. For example, the gas sensor 34 reads 10% methane, the processor can open valve 392 in order to bleed the methane out of the surgical cavity. In this example, the system 300 would need to be used alongside either an entirely separate insufflator or an external insufflator that is connected via some communication. In this example, the smoke evacuator shown in FIG. 3 detects the methane, opens valve 392 to bleed the methane off, which creates an under pressure that the insufflator will sense and flow in carbon dioxide to compensate. That is one example of taking corrective action in response to a gas species being present and/or outside of a desired range.

Figure 4:
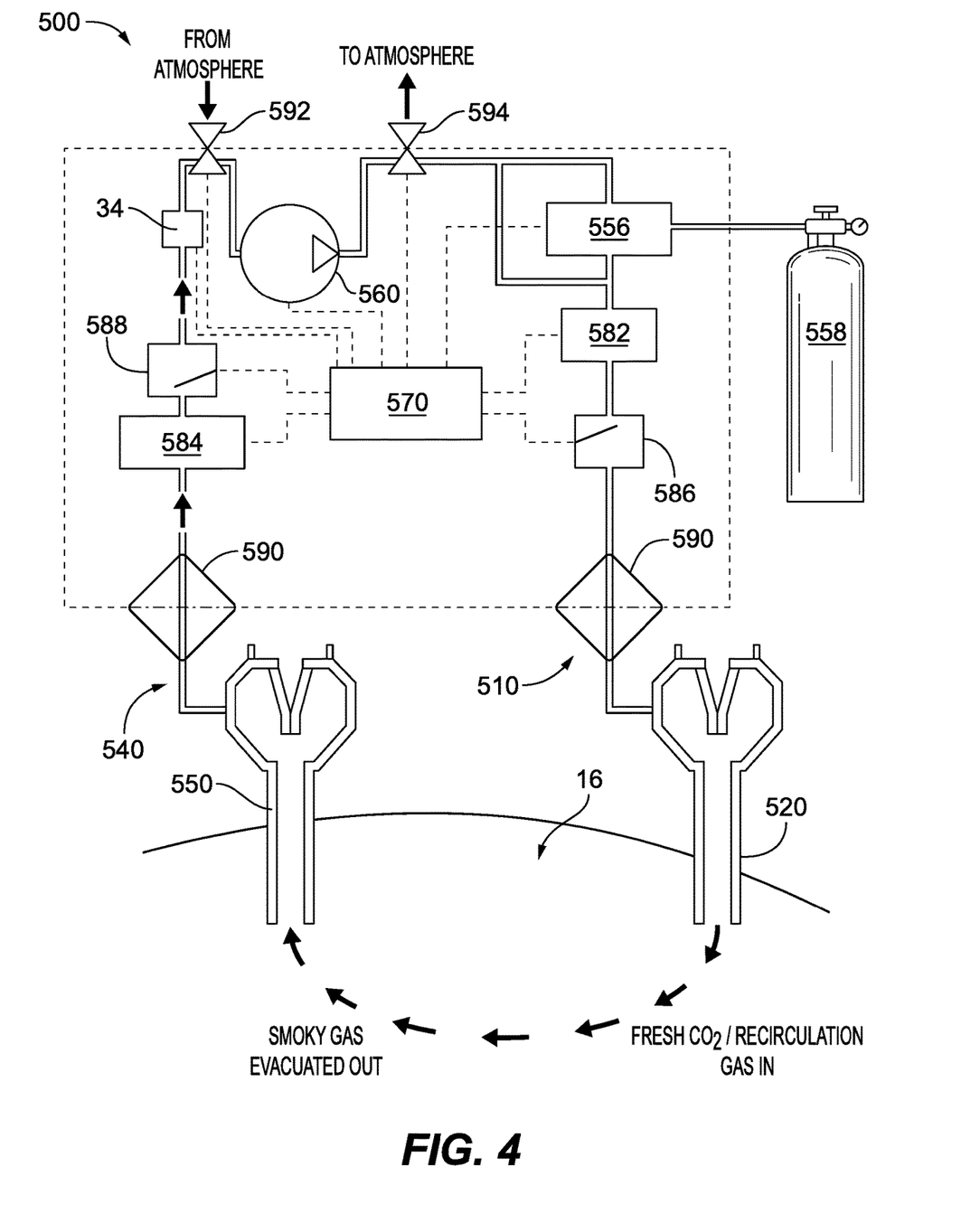
FIG. 4 is a schematic illustration of a surgical gas delivery system constructed in accordance with another embodiment of the subject disclosure which is configured for continuous monitoring of gas species in a flow of gas from a surgical cavity during smoke evacuation with venting and an integrated insufflator.

Referring now to FIG. 4, there is illustrated a smoke evacuation system with venting and integrated insufflator for continuously removing gas from a surgical cavity 16 of a patient during an endoscopic surgical procedure, which is designated generally by reference numeral 500. Smoke evacuation system 500 includes flow rate and/or pressure sensors 584, 588 that are associated with the inlet flow path 540 of the vacuum pump 560 leading from trocar 550, and it includes flow rate and/or pressure sensors 582, 586 that are associated with the insufflation path 510 leading to trocar 520, as well as filters 590. In this regard, it should be understood that while the flow of gas throughout this system 500 is essentially continuous, there may be circumstances in which the insufflation or gas delivery flow rate and/or the evacuation or gas removal flow rate could temporarily drop to 0 L/min, in order to prevent extreme under or over pressure conditions in the system 500.

In addition, in smoke evacuation system 500, an outlet side of the pump 560 communicates with the insufflation flow path 510, downstream from the insufflation unit 556 which is connected to insufflation gas source 558. Furthermore, a valve 592 is associated with an inlet side of the pump 560 and it is controlled by the processor 570 to draw in gas from atmosphere, and/or an exhaust valve 594 is located on the outlet side of the pump 560 and is controlled by the processor 570 to bleed off gas to atmosphere as an example of taking corrective action, similar to that described above with respect to FIG. 3. As a result of this plumbing arrangement, the outlet flow path or pressure circuit 510 of smoke evacuation system 500 may be augmented with an incoming flow of fresh insufflation gas, if necessary.

Similar to system 10 described above, system 500 includes a sensor 34 in the flow path 540 just upstream of the valve 592 and pump 560 and just downstream from flow sensors 584 and 588 for monitoring a plurality of gas species in the gas flow from the surgical cavity 16. Sensor 34 is operatively connected to the processor 570 for control of gas composition in the surgical cavity 16.

Figure 5:
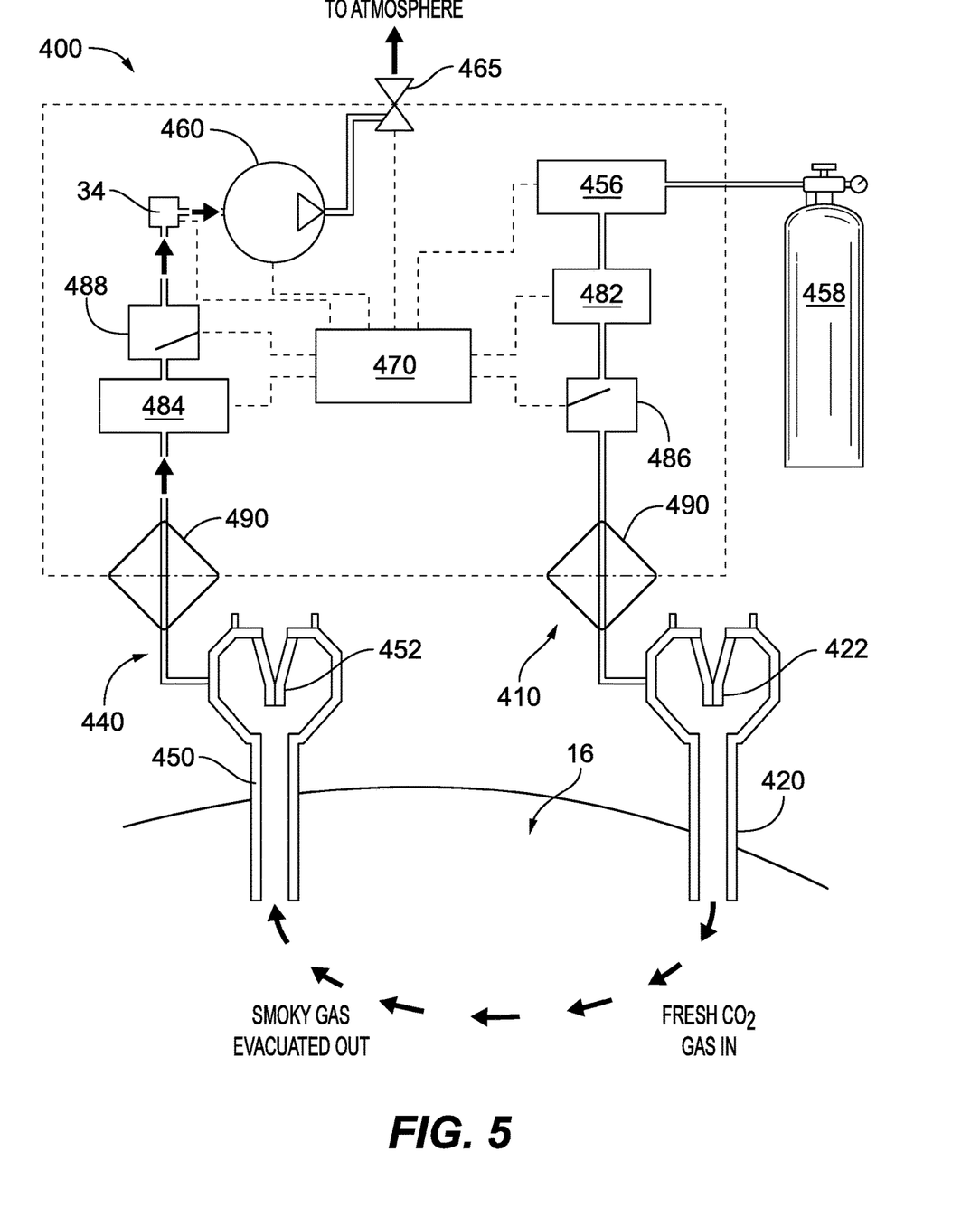
FIG. 5 is a schematic illustration of a surgical gas delivery system constructed in accordance with another embodiment of the subject disclosure which is configured for continuous monitoring of gas species in a flow of gas from a surgical cavity during smoke evacuation with pneumatically independent insufflation and suction circuits.

Referring to FIG. 5, there is illustrated a system 400 with smoke evacuator and pneumatically-independent insufflation and suction circuits. Smoke evacuation system 400 can utilize an insufflation/sense line that alternates between insufflating gas and sensing cavity pressure, or it could utilize real time pressure monitoring as disclosed in U.S. patent application Ser. No. 15/812,649 or 15/945,007, each of which is incorporated by reference herein in its entirety.

Smoke evacuation system 400 includes an inlet flow path 410 leading to a first trocar 420 communicating with the surgical cavity 16 through which a continuous flow of clean gas is delivered to the surgical cavity 16. The first trocar 420 is preferably a standard trocar with a mechanical seal 422. The system 400 further includes an outlet flow path 440 leading from a second trocar 450 communicating with the surgical cavity 16 though which a continuous flow of smoky gas is evacuated from the surgical cavity 16. The second trocar 450 is also preferably a standard trocar with a mechanical seal 452. An insufflation unit 456 communicates with the inlet flow path 410 for delivering a continuous flow of clean gas to the surgical cavity 16. The insufflation unit 456 is operatively connected to a gas source 458, which can be an independent storage tank 458 or house gas from a main distribution line.

A vacuum pump 460 communicates with the outlet flow path 440 for removing a continuous flow of smoky gas from the surgical cavity 16. The vacuum pump 460 is operatively connected to an exhaust valve 465, which preferably vents filtered gas to atmosphere. A processor 470 controls both the insufflation unit 456 and the pump 460 (as well as valve 465) in such a manner so that clean gas is delivered to the surgical cavity 16 by the insufflation unit 456 at a gas flow rate that relates to the gas flow rate at which smoky gas is removed from the surgical cavity 16 by the vacuum pump 460.

For example, the processor 470 controls both the insufflation unit 456 and the vacuum pump 460 in such a manner so that clean gas is delivered to the surgical cavity 16 by the insufflation unit 456 at a gas flow rate that is equal to the gas flow rate at which smoky gas is removed from the surgical cavity 16 by the pump 460, or at a gas flow rate that is greater than or less than the gas flow rate at which smoky gas is removed from the surgical cavity 16 by the pump 460, in the event of an under-pressure condition or an over-pressure condition in the surgical cavity 16. In this regard, it should be understood that while the flow of gas throughout this system is essentially continuous, there may be circumstances in which the insufflation or gas delivery flow rate and/or the evacuation or gas removal flow rate could temporarily drop to 0 L/min, in order to prevent extreme under or over pressure conditions in the system. Preferably, a filter 490 is operatively associated with at least one of the inlet flow path 410 and the outlet flow path 440, for cleaning or otherwise condition the gas passing therethrough.

The system 400 may be configured so that the gas flow rate, supplied at a programmed driving pressure, varies depending upon a surgical cavity pressure within the surgical cavity 16. The processor 470 is configured to determine the surgical cavity pressure corresponding to a gas flow rate measurement continuously measured by a flow sensor communicating with processor 470, such as, for example, the flow sensor 482 operatively associated with the inlet flow path 410 and/or the flow sensor 484 operatively associated with the outlet flow path 440. A typical driving pressure for a smoke evacuation system of this type is about 60 mmHg.

The system 400 may be configured so that a driving pressure required to maintain a specified gas flow rate varies depending upon a surgical cavity pressure in surgical cavity 16 and the processor 470 is configured to determine the surgical cavity pressure corresponding to a measured driving pressure continuously measured by a flow sensor communicating with processor 470, such as, for example, the pressure sensor 486 operatively associated with the inlet flow path 410 and/or the pressure sensor 488 operatively associated with the outlet flow path 440. A typical gas flow rate for a smoke evacuation system of this type is about 5 L/min. Those skilled in the art will readily appreciate that system 200 can be used for smoke evacuation, additional details of which are described in U.S. patent application Ser. No. 15/945,007, which is incorporated by reference herein in its entirety.

System 400 includes a sensor 34 in the flow path 440 just upstream of the valve 465 and pump 460 and just downstream from flow sensors 484 and 488 for monitoring a plurality of gas species in the gas flow from the surgical cavity 16. Sensor 34 is operatively connected to the processor 470 for control of gas composition in the surgical cavity 16. System 400 can control the exhaust valve/insufflation rate to combat a gas composition reading out of the desired range, as an example of taking corrective action. For example, in this embodiment, if the sensor 300 detects the presence of an undesired gas species and/or a gas species that is outside of a desired range, the processor 470 can cause the evacuation pump 460 and valve 465 to evacuate more and can cause the insufflator to insufflate more to make up for the evacuated gas.

Figure 6:
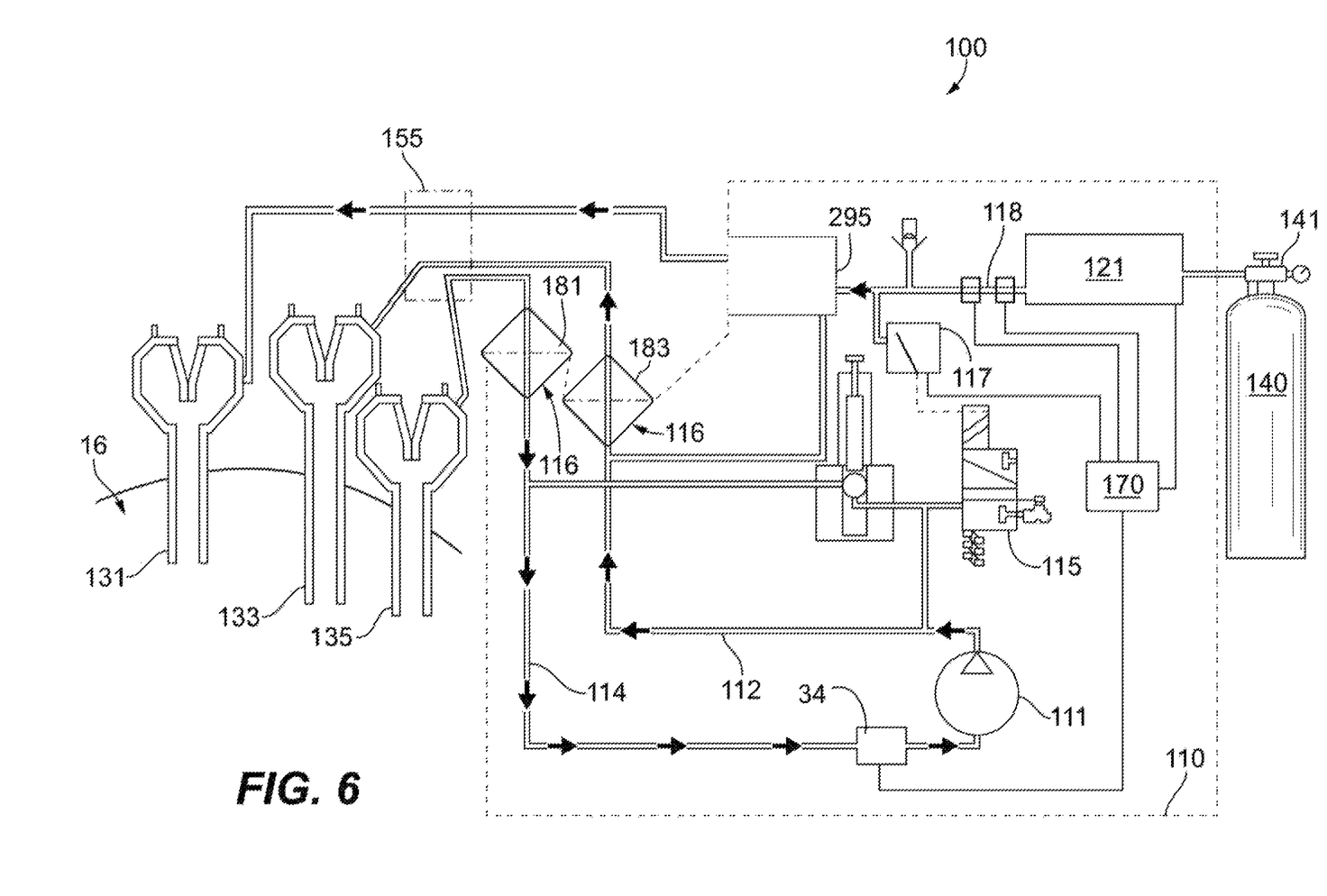
FIG. 6 is a schematic illustration of a multimodal surgical gas delivery system constructed in accordance with an embodiment of the subject disclosure which is configured for monitoring gas species in a flow of gas from a surgical cavity with a pneumatically-sealed valveless trocar.

As shown in FIG. 6, a gas delivery system 100 is provide as a multi-modal insufflation system configured to run a pneumatically-sealed valveless trocar. The system 100 is adapted to function with three surgical access devices or trocars (131, 133, 135) that are in communication with a patient's surgical cavity 16. It is envisioned that gas delivery system 100 can also be used with two surgical access devices or trocars, as disclosed for example in commonly assigned U.S. Pat. No. 9,375,539. Alternatively, the system can be employed with a single surgical access device as disclosed for example in commonly assigned U.S. Pat. No. 9,295,490. System 100 includes a control unit 110 similar to control unit 210 described above, wherein similarly numbered items in control unit 110 of FIG. 6 are the same as those described above with respect to control unit 210 of FIG. 2, which is connected to a pressure source 140 by way of a pressure regulator 141.

A tube set 155 is also provided and it is adapted and configured to connect at one end to the supply conduit 114, return conduit 112 and insufflation conduit 118, and at the opposing end to the surgical access devices 131, 133, 135, which are in fluid communication with the surgical cavity 16. The configuration of the tube set 155 can vary, depending on the desired implementation. In the case of the system 100, the tube set 155 preferably has a unitary, multi-lumen connection to input 181 and output 183 ports or interfaces, and separate connections to the individual surgical devices 131, 133, 135. It is envisioned that the tube set 155 can have a compound, multi-lumen tube, beginning at the connections to the ports 181, 183 for a predetermined distance from the control unit 110, and at an intermediate point of bifurcation (e.g. in the schematic box of tube set 155 in FIG. 6) yields multiple separate tubes. In the case of the system 100, three separate tubes, separately lead to each of the surgical devices 131, 133, 135, which may be surgical access devices with insufflation capability, or other instruments, such one or more veress needles. The surgical devices 131, 133, 135 are thus individually connected to one of the supply conduit 114, return conduit 112 and insufflation conduit 118, and therefore respectively facilitate that function. While not shown separately, those skilled in the art will readily appreciate that valve 295 can include an interface similar to ports 181 and 183 but for the tube set 155 to connect to conduit 118 to surgical device 131.

As set forth above, in one preferred aspect, the separate distal tube portions of the tube set 155 are connected by way of a conventional fitting, such as a luer-lock fitting on a conventional surgical device. The precise configuration of the tube set 155 can vary depending on the desired configuration. An example of a fitting for a multi-lumen tube set is described in commonly assigned U.S. Pat. No. 9,526,886, the disclosure of which is herein incorporated by reference in its entirety.

A disposable filter 116 is also associated with the tube set 155, either separate therefrom or integral therewith, e.g. at each port 181, 183, and the port or interface of the valve 295. A filter suitable for use with a multimodal gas delivery system 100 with insufflation, smoke evacuation and recirculation functionality for use with specialized pneumatically sealed surgical access devices is disclosed in U.S. Pat. Nos. 9,067,030 and 9,526,849, the disclosures of which are herein incorporated by reference in their entireties.

System 100 includes a sensor 34 similar to that described above with respect to FIG. 1 in the flow path of supply conduit 114 just upstream of the pump 111 for monitoring a plurality of gas species in the gas flow from the surgical cavity 16. Sensor 34 is operatively connected to the processor 170 for control of gas composition in the surgical cavity 16, much like processor 170 described above with reference to FIG. 2. This allows for monitoring the gas composition within the body cavity of a patient during a surgical procedure, for example so that any undesirable changes in gas composition can be corrected.

A method for controlling gas composition in a surgical cavity (e.g. surgical cavity 16 of FIGS. 1-6) during an endoscopic surgical procedure includes monitoring for a plurality of gas species in a gas flow from a surgical cavity of a patient, e.g., monitoring the gas flow in any of flow path 24, conduit 114, flow path 340, flow path 540, and flow path 440 described above. The method includes measuring the plurality of gas species in the gas flow from the surgical cavity and determining if the gas species measured in the gas flow from the surgical cavity are each are present and/or within a respective desired range, e.g. using a sensor 34 as described above in fluid communication with the gas flow from the surgical cavity. The method includes taking corrective action in any of the gas species are outside the respective desired range.

Taking corrective action can include adding gas, e.g., from a source 140, 558, or 458 as described above, into the surgical cavity if one or more gas species in the plurality of gas species is outside of the respective desired range, e.g., so as to bring a composition of gas species in the surgical cavity within the respective desired range. This allows for maintaining multiple gas species within their desired range during a surgical procedure. Taking corrective action can include warning a user of non-ideal gas composition. Taking corrective action can include instructing an external or internal insufflator to flush the surgical cavity with carbon dioxide. Taking corrective action can include removing non-ideal gas from the cavity via suction or smoke evacuation mechanisms. Taking corrective action can include disabling a device, such as an electrocautery or anesthesia device, to prevent harm to the patient.

Monitoring for a plurality of gas species in a gas flow from the surgical cavity can involve continuously monitoring the flow of gas, however it is also contemplated that monitoring for a plurality of gas species in a gas flow from the surgical cavity can involve periodically sampling the flow of gas. For example, a system can take a measurement of the whole gas flow at time 0, then let 30 seconds pass, and take another measurement. In another example, a system can take constant (or nearly constant) measurements of a side stream that is diverted from the main gas flow path and measure from the side stream. Moreover, any combination of periodic or continuous monitoring can be used with any combination of in line or side stream sampling.

The gas flow from the surgical cavity can result from evacuating gas from the surgical cavity, from recirculating gas from the surgical cavity, and/or from intermittently leaking gas from the surgical cavity. Adding gas into the surgical cavity can involve delivering a flow of gas into the surgical cavity from an insufflator, e.g. using an insufflation subunit 121, 556, or 456 as described above.

This method can include determining if the composition of gas species includes a concentration of Carbon Dioxide ($CO_2$) that is below a specified level, and adding Carbon Dioxide ($CO_2$) into the surgical cavity if the concentration of Carbon Dioxide ($CO_2$) is below the specified level so to increase the concentration of Carbon Dioxide ($CO_2$) in the surgical cavity above the specified level. However, those skilled in the art will readily appreciate that monitoring for a plurality of gas species and determining if the gas species measured are in range can include monitoring for and determining if any other suitable gas species is present, and in what concentration. For example, systems and methods disclosed herein can monitor the gas flow for Nitrogen ($N_2$), Oxygen ($O_2$), Nitrous Oxide ($N_2O$), water vapor ($H_2O$), Sevoflurane, Methane ($CH_4$), Xenon (Xe), Argon (Ar), Desflurane, Isoflurane, volatile organic compounds (VOC) and/or Carbon Monoxide (CO). For example, if oxygen and a combustible gas such as carbon monoxide or methane are out of the desired range, the system 10 can warn surgical personnel and the gas composition can be corrected before any surgical tools like electrocautery devices that could combust the gas mixture are introduced. As another example, if the amount of an anesthetic such as Nitrous Oxide, Sevoflurane, Desflurane, or Isoflurane is out of the desired range, the system 10 can warn the surgical personnel that the anesthesia may need to be corrected. In another example, if room air enters the surgical cavity from leakages or from gas trapped in sterile tubesets or other medical products pneumatically sealed in sterile packaging and then inserted or attached to the bodily cavity, the nitrogen and/or oxygen levels may be out of the desired range which can be corrected, for example by supplying pressurized carbon dioxide to flush out the nitrogen and oxygen in the surgical cavity to avoid embolism.

Figure 7A:
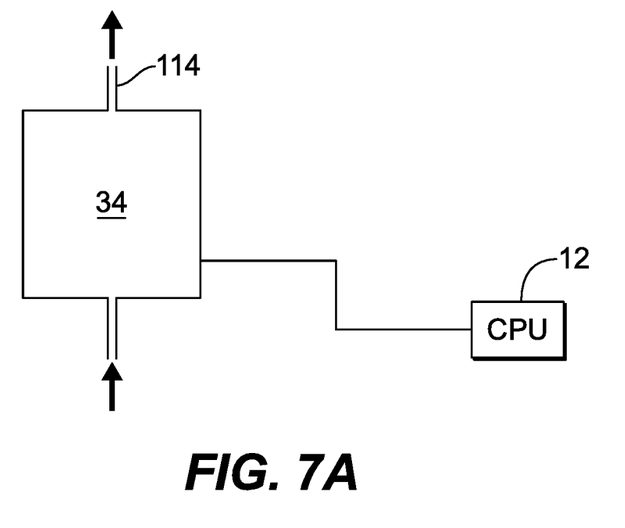
FIG. 7A is a schematic illustration of an exemplary embodiment of a gas sensor constructed in accordance with the subject disclosure, with a gas species sensor in-line with the flow path of the gas flow from the surgical cavity.
Figure 7B:
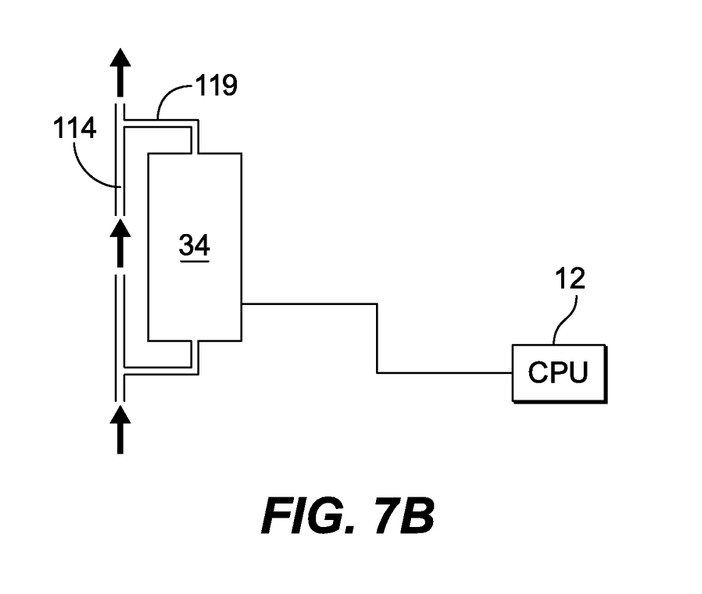
FIG. 7B is a schematic illustration of an exemplary embodiment of a gas sensor constructed in accordance with the subject disclosure, with a gas species sensor positioned in a parallel flow path meant to sample from the main flow path of the gas flow from the surgical cavity.

With reference now to FIG. 7A, sensor 34 is shown as a single, multi-gas sensor in line with conduit 114 and connected to processor 12, as described above with respect to FIG. 2. It is also contemplated that sensor 34 can be a multi-gas sensor connected in parallel with the conduit 114 as shown in FIG. 7B where the sensor 34 is connected in fluid communication with the gas flow through the conduit 114 through a bypass conduit 119. In short, a sensor 34 can be included in any system as described above, anywhere in the system on the side of the outlet from the surgical cavity, e.g., anywhere in conduit 114 upstream of the pump 111 in FIG. 2.

Figure 8A:
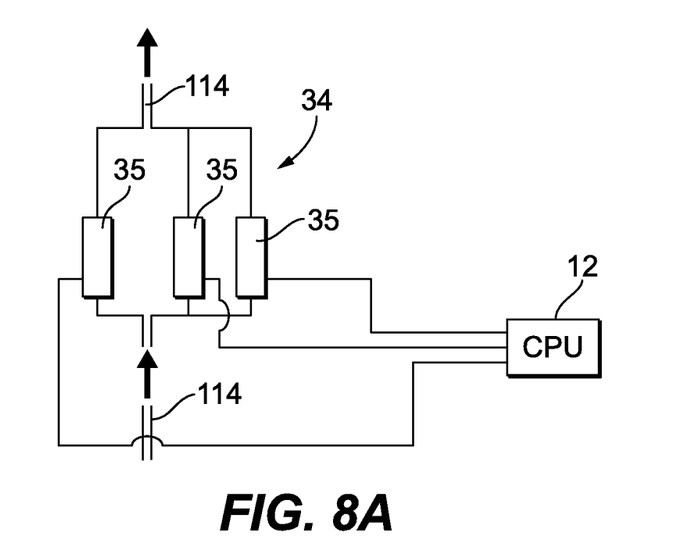
FIG. 8A is a schematic illustration of an exemplary embodiment of a gas sensor constructed in accordance with the subject disclosure, with an array having a plurality of gas species sensors connected in parallel to one another, wherein the array is connected in-line with the flow path of the gas flow from the surgical cavity.
Figure 8B:
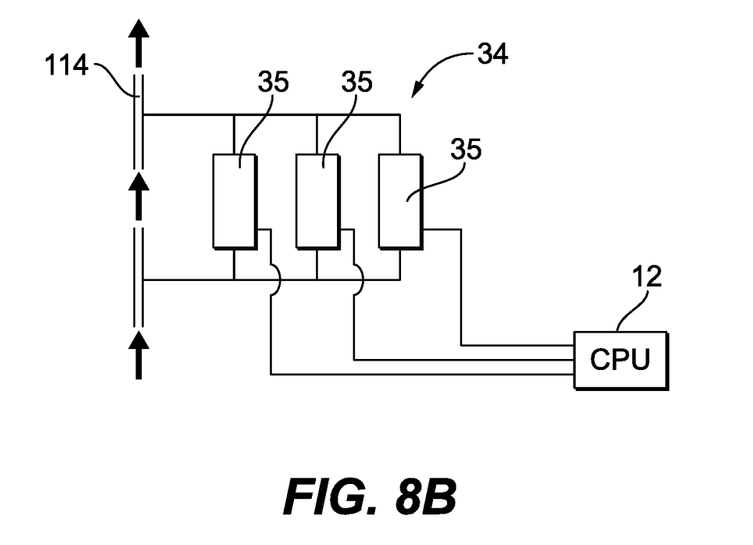
FIG. 8B is a schematic illustration of an exemplary embodiment of a gas sensor constructed in accordance with the subject disclosure, with an array having a plurality of gas species sensors connected in parallel to one another, wherein the array is connected in a parallel flow path meant to sample from the main flow path of the gas flow from the surgical cavity.

With reference now to FIG. 8A, it is also contemplated that the sensor 34 can include an array of gas species sensors 35, e.g., where each gas species sensor 35 is sensitive to one or more different gas species unique from the other gas species sensors 35 in the array. Each of the gas species sensors 35 is operatively connected to the processor 12 to provide input indicative of the amount of a respective species of gas in the gas flow through the conduit 114. As shown in FIG. 8A, the array of gas species sensors 35 is as a whole in line with the conduit 114, and each of the gas species sensors 35 is in parallel with the others. FIG. 8B shows another arrangement of the gas species sensors 35 wherein the array as a whole is in parallel with the conduit 114, and wherein each respective sensor 35 is in parallel with the others.

Some gas sensors measure percentage of a concentration of a particular gas species. For example, if there is 20% carbon dioxide in a gas composition, a combination sensor can read the flow of gas passing through it and determine that the gas composition it is 20% carbon dioxide, 70% oxygen, and 10% water vapor, e.g., on a molar basis. The gas sensors may measure mass flow rates or volumetric flow rates in order to measure the presence of different gas species. The system/method may include the use of a look-up table to calculate molar percentages from a plurality of mass flow or volumetric flow readings.

In another aspect, especially with the arrays of single-gas sensors, each single sensor can provide a reading for a given gas species. For example, sensor A may read 2 Liters/min of carbon dioxide, sensor B may read 7 Liters/min of oxygen, and sensor C may read 1 L/min of water vapor, all for the same composition of gas flowing through a main flow path. In this type of configuration, the processor can aggregate information from the different sensors in order to calculate percentages, e.g., on a molar basis. This can be done either by summing the totals of all the mass or volumetric flow rates measured by all the sensors, or it can be done by including an in-line flow meter to determine the overall mas or volumetric flow rate. The processor can calculate molar percentages via a look up table or other information stored or pre-programmed into the system. This information can include molar masses or calibration data for the sensors in the array.

Figure 9A:
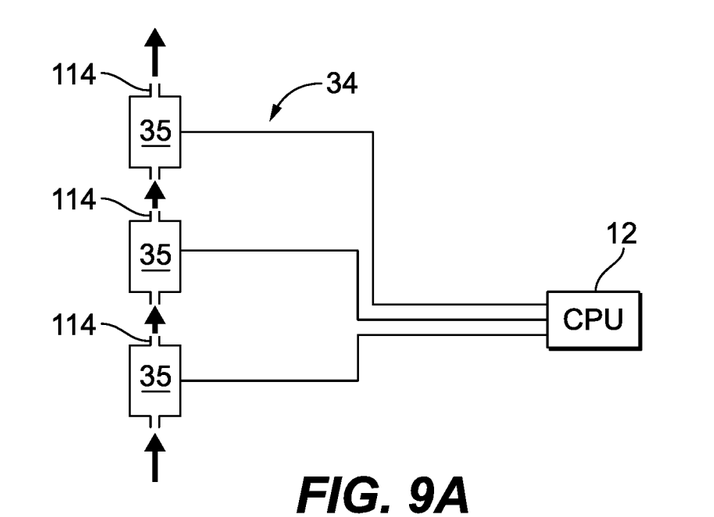
FIG. 9A is a schematic illustration of an exemplary embodiment of a gas sensor constructed in accordance with the subject disclosure, with an array having a plurality of gas species sensors connected in series with one another, wherein the array is connected in-line with the flow path of the gas flow from the surgical cavity.
Figure 9B:
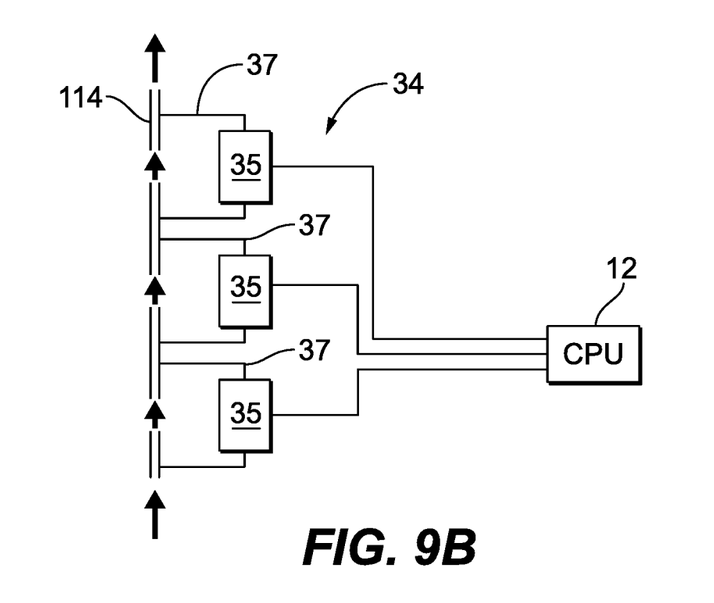
FIG. 9B is a schematic illustration of an exemplary embodiment of a gas sensor constructed in accordance with the subject disclosure, with an array having a plurality of gas species sensors arranged in series with each sensor connected in a parallel flow path meant to sample from the main flow path of the gas flow from the surgical cavity.

In embodiments such as in FIGS. 7B, 8B, and 9B, there is an array of sensors that sample off of the main flow path. This side sample path will have a smaller flow rate than the main flow path, and that flow rate can be measured and used to calculate gas composition percentages, e.g., on a molar basis, alongside the readings of each individual gas sensor in the array. The processor may include a calculation on how the pneumatics of the flow paths affect gas composition in the side stream in order to more accurately calculate overall gas composition.

With reference now to FIG. 9A, it is also contemplated that the array of a multi-species sensor 34 can be arranged with the individual gas species sensors 35 each in direct series with each other and in-line with the conduit 114. In another arrangement, shown in FIG. 9B, the array of a multi-species sensor 34 can be arranged with each individual gas species sensor 35 in its own bypass flow line 37 in parallel with the flow through the conduit 114, wherein the gas species sensors 35 (each with its respective bypass flow line 37) are spaced out in series along the conduit 114. While FIGS. 8A, 8B, 9A, and 9B each show three gas species sensors 35, those skilled in the art will readily appreciate that any suitable number of gas species sensors 35 can be included without departing from the scope of this disclosure, and that each gas species sensor 35 can be sensitive to a single gas species or to multiple gas species. For example, a multi-gas species sensor can be networked together with a single gas species sensor. FIGS. 1-6 show various examples of systems that can utilize sensors 34, and each can be used with any of the configurations of sensor 34 shown in FIGS. 7A-9B.

The methods and systems of the present disclosure, as described above and shown in the drawings, provide for control of gas composition in a surgical cavity with superior properties including the ability to monitor for multiple different gas species. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A method for controlling gas composition in a surgical cavity during an endoscopic surgical procedure, comprising:
   a) monitoring for a plurality of gas species in a gas flow from the surgical cavity of a patient, wherein the gas flow is driven by a pump, wherein monitoring includes using an array of gas species sensors that is positioned to sample from a stream of gas flow parallel with a main gas flow coming from the surgical cavity, upstream of the pump, wherein the stream of gas flow parallel to the main gas flow branches off of the main gas flow upstream of the array of gas species sensors and rejoins the main gas flow downstream of the array of gas species sensors;
   b) measuring the plurality of gas species in the parallel stream of gas flow from the surgical cavity using the array of gas species sensors;
   c) determining if the plurality of gas species measured in the gas flow from the surgical cavity are each present and/or within a respective desired range; and
   d) taking corrective action if any of the plurality of gas species are outside the respective desired range.

2. The method according to claim 1, wherein taking corrective action includes adding gas into the surgical cavity if one or more gas species in the plurality of gas species is outside of the respective desired range so as to bring a composition of gas species in the surgical cavity within the respective desired range.

3. The method according to claim 1, wherein taking corrective action includes warning a user of non-ideal gas composition.

4. The method according to claim 1, wherein taking corrective action includes instructing an insufflator to flush the surgical cavity with carbon dioxide.

5. The method according to claim 1, wherein taking corrective action includes disabling a device to prevent harm to the patient.

6. The method according to claim 1, wherein monitoring for a plurality of gas species in a gas flow from the surgical cavity involves continuously monitoring the flow of gas.

7. The method according to claim 1, wherein monitoring for a plurality of gas species in a gas flow from the surgical cavity involves continuously or periodically sampling the flow of gas.

8. The method according to claim 1, wherein the gas flow from the surgical cavity results from evacuating gas from the surgical cavity.

9. The method according to claim 1, wherein the gas flow from the surgical cavity results from recirculating gas from the surgical cavity.

10. The method according to claim 1, wherein the gas flow from the surgical cavity results from intermittently leaking gas from the surgical cavity.

11. The method according to claim 1, wherein taking corrective action includes delivering a flow of gas into the surgical cavity from an insufflator or gas recirculator.

12. The method according to claim 1, wherein determining if the plurality of gas species measured in the gas flow from the surgical cavity are each within a respective desired range involves determining if a composition of gas species includes a concentration of Carbon Dioxide ($CO_2$) that is below a specified level.

13. The method according to claim 12, wherein adding gas into the surgical cavity involves adding Carbon Dioxide ($CO_2$) into the surgical cavity if the concentration of Carbon Dioxide ($CO_2$) is below the specified level so to increase the concentration of Carbon Dioxide ($CO_2$) in the surgical cavity above the specified level.

14. The method according to claim 1, wherein monitoring for a plurality of gas species and determining if the gas species measured includes monitoring for and determining if Nitrogen ($N_2$) is within a respective desired range.

15. The method according to claim 1, wherein monitoring for a plurality of gas species and determining if the gas species measured includes monitoring for and determining if Oxygen ($O_2$) is within a respective desired range.

16. The method according to claim 1, wherein monitoring for a plurality of gas species and determining if the gas species measured includes monitoring for and determining if Nitrous Oxide ($N_2O$) is within a respective desired range.

17. The method according to claim 1, wherein monitoring for a plurality of gas species and determining if the gas species measured includes monitoring for and determining if water vapor ($H_2O$) is within a respective desired range.

18. The method according to claim 1, wherein monitoring for a plurality of gas species and determining if the gas species measured includes monitoring for and determining if Sevoflurane is within a respective desired range.

19. The method according to claim 1, wherein monitoring for a plurality of gas species and determining if the gas species measured includes monitoring for and determining if Methane ($CH_4$) is within a respective desired range.

20. The method according to claim 1, wherein monitoring for a plurality of gas species and determining if the gas species measured includes monitoring for and determining if one or more of Xenon (Xe), Argon (Ar), Desflurane, Isoflurane, and/or Carbon Monoxide (CO) is within a respective desired range.

21. The method according to claim 1, wherein measuring the plurality of gas species in the gas flow includes calculating each gas species as a molar percentage.

22. The method according to claim 21, wherein calculating each gas species includes calculating each gas species as a molar percentage by summing flow rates of individual gas species based on information from the array of gas species sensors and dividing by total flow rate for all gas species in the gas flow.

* * * * *